United States Patent [19]
Mirzabekov et al.

[11] Patent Number: 5,981,734
[45] Date of Patent: Nov. 9, 1999

[54] METHODS FOR IMMOBILIZING NUCLEIC ACIDS ON A GEL SUBSTRATE

[75] Inventors: Andrei Darievich Mirzabekov, Moscow; Dimitri Y. Proudnikov, Samara; Edward N. Timofeev, Moscow; Svetlana V. Kochetkova, Moscow; Vladimir L. Florentiev, Moscow; Valentine V. Shick, Moscow, all of Russian Federation

[73] Assignee: University of Chicago, Chicago, Ill.

[21] Appl. No.: 08/895,656

[22] Filed: Jul. 17, 1997

[51] Int. Cl.⁶ .......................... C07H 21/00; C07H 21/04; C08F 120/56
[52] U.S. Cl. .................. 536/25.3; 536/25.31; 536/25.32; 428/41.5
[58] Field of Search ................. 536/25.3, 25.31, 536/25.32; 428/41.5

[56] References Cited
PUBLICATIONS

Fatty et al. Nucl. Acids Res. 21(8): 1819–1826, 1993.

Timofeev, et al. Regioselective immobilizaton of short oligonucleotides to acrylic copolymer gels, vol. 24, pp. 3142–3148. (1996 Nucleic Acids Research).

Proudnikov, et al. "Chemical methods of DNA and RNA fluorescent labeling". Vol. 24, pp. 4535–4542. (1996 Nucleic Acids Research).

*Primary Examiner*—Gary L. Kunz
*Attorney, Agent, or Firm*—Cherskov & Flaynik

[57] ABSTRACT

A method for labeling oligonucleotide molecules, and for immobilizing oligonucleotide and DNA molecules is provided comprising modifying the molecules to create a chemically active group, and contacting activated fluorescent dyes to the region. A method for preparing an immobilization substrate is also provided comprising modifying a gel to contain desired functional groups which covalently interact with certain moieties of the oligonucleotide molecules. A method for immobilizing biomolecules and other molecules within a gel by copolymerization of allyl-substituted oligonucleotides, DNA and proteins with acrylamide is also provided.

10 Claims, 8 Drawing Sheets i: Me₂CO,TsOH, AZEOTROPIC REMOVE OF WATER,
ii: MsCl, Py;
iii: LiN₃,DMF, 150°C
iv: Ph₃P, NH₄OH;
v: AcrCl, TEA, 0°C

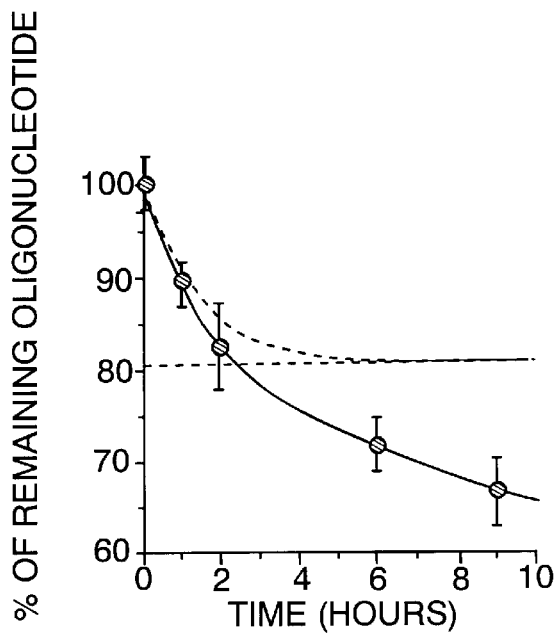
Fig. 8A
Fig. 8B
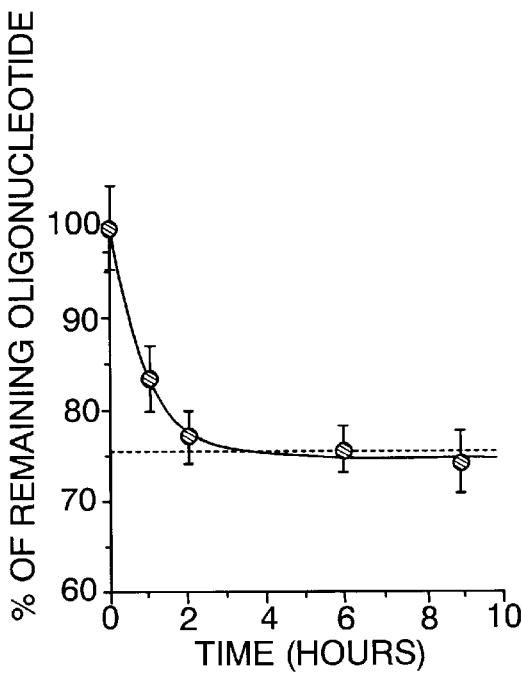
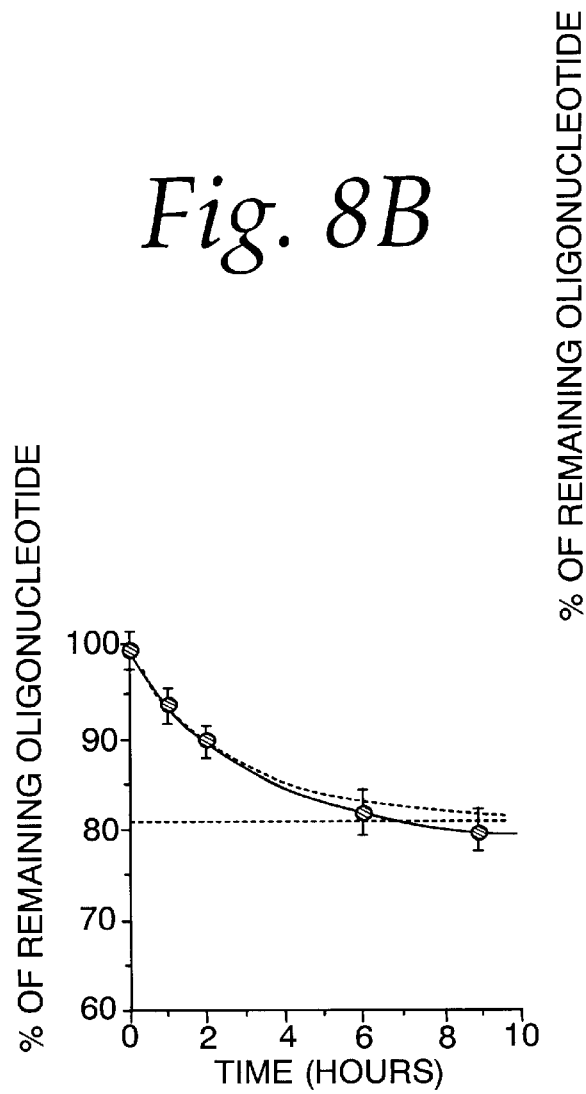
Fig. 8C 5,981,734

METHODS FOR IMMOBILIZING NUCLEIC ACIDS ON A GEL SUBSTRATE

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to methods for modifying nucleic acid molecules for their later manipulation and, more particularly, this invention relates to methods for labeling modified nucleic acid molecules or for immobilizing modified nucleic acid molecules on to specified supports.

2. Background of the Invention

Manipulating nucleic acids for subsequent use and analysis is increasing in importance. For example, the labeling of polynucleotides for later use as indicators of complementary sequences in target molecules has wide utility in diagnostic and research applications. Also, designing polynucleotides to interact with inert substrates such as activated polyacrylamide gels will increase the utility of labeling and sequencing activities.

Present techniques for labeling and/or immobilizing nucleic acids have several drawbacks. Labeling processes will be discussed first.

Three widely-accepted methods exist for the labeling of molecules: radio-labeling, fluorescent-labeling, and chemiluminescent labeling. There are benefits to each method. Radio-labels are more sensitive. Fluorescent labels are safer, can be detected in real time, and several different labels can be simultaneously monitored. Chemiluminescent labels have the same sensitivity as radio-labels, and are also safer, but can only be used once.

The most commonly used process for fluorescent labeling of nucleic acids involves enzymatic reactions. Typically, organic fluorophores are first chemically introduced into PCR oligonucleotide primers or nucleoside triphosphates and then incorporated by using DNA or RNA polymerases (via the use of polymerase chain reaction processes, or terminal polynucleotide transferase). These techniques are expensive and not always efficient and reliable. Also, some labelling processes result in obfuscating or breaking the continuity of a target oligonucleotide sequence on the labeled molecule during polymerase reactions. As such, less accurate duplexes form when sequencing DNA strands via hybridization procedures.

As noted above, methods for immobilizing nucleic acids and related molecules also have drawbacks. Oligonucleotides can be immobilized by reacting their 3'-dialdehyde termini (produced through chemical treatment with the oligos) with hydrazide groups located on gel support compounds. Unfortunately, typical hydrazide chemistry protocols require preactivation of oligonucleotides, and also result in attachment bonds which are not resistant to repeated hybridization processes.

A need exists in the art to provide modified nucleotides which can interact with labels and high volume supports. A need also exists to provide efficient and inexpensive methods to label and otherwise examine synthetically-derived, or naturally-occurring nucleotide molecules of any length. The methods and resulting modified molecules must be compatible with hybridization occurrences between the labeled polynucleotide and non-labeled polynucleotides. The methods also should allow for the incorporation of different labels into a nucleic acid fragment for multi-color hybridization analysis. Lastly, the methods should facilitate chemical coupling, or photopolymerization of modified molecules, such as polynucleotides, with high volume supports such as gel substrates.

SUMMARY OF THE INVENTION

It is an object of the present invention to provide methods for preparing molecules for labeling or other manipulation that overcomes the disadvantages of the prior art.

Another object of the present invention is to provide a method for modifying molecules for subsequent analysis. A feature of the method is that the modification facilitates bonding of the molecules throughout a high volume support such as a gel substrate. An advantage of the method is that the molecules can be chemically modified to facilitate bonding or photopolymerized with moieties of the support so as to enhance the capacity of the support to accommodate the molecules and reactions associated with the molecules.

Yet another object of the present invention is to provide methods for labeling polynucleotide molecules of any length. A feature of the invention is the chemical modification of a terminus or an internal residue of the molecules for subsequent attachment of different labels. An advantage of the invention is that the efficiency of the labeling is independent of the oligonucleotide length.

Still another object of the present invention is to provide a method for chemically labeling biomolecules. A feature of the invention is direct fluorescent labeling of DNA and RNA. An advantage of the invention is that the labeling method can be applied to both DNA and RNA, either isolated from cells or synthesized. An additional advantage is that the method is compatible with DNA and RNA fragmentation techniques, in as much as the amount of introduced label does not depend on the length of a target oligonucleotide sequence.

Another object of the present invention is to provide a method for facilitating the immobilization of molecules, such as polynucleotides and proteins, to a high volume support such as a gel substrate. A feature of the invention is that the support contains functional groups throughout its matrix, whereby the functional groups are attracted to functional groups contained on the molecules. An advantage of the invention is a rapid diffusion of oligonucleotides throughout the substrate thereby enhancing the capacity of the substrate to accommodate large amounts of molecules for subsequent manipulation of the molecules.

A further object of the present invention is to provide a method for immobilizing oligonucleotides. A feature of the invention is juxtaposing functional groups of oligonucleotides to functional groups on molecules located throughout an immobilizing support, and then modifying the support to both activate the functional groups thereon and effect bonding between the oligonucleotides and the support. An advantage of the method is the production of an oligo-support complex capable of withstanding multiple hybridization cycles.

In brief, the objects and advantages of the present invention are achieved by a method for labeling nucleic acid molecules comprising modifying the nucleic acid molecules to create a region having an active center; and contacting a dye to the active center so as to cause attachment of said dye to the active center. One embodiment of the method is modifying the molecules to create a nucleophilic region (e.g., a region containing a primary amino group) or an electrophilic region (e.g., a region containing a carbonyl group); and contacting an activated fluorescent dye with the region so as to cause addition of the fluorescent label to the region.

The invention also provides a method for immobilizing oligonucleotide molecules comprising supplying a support containing functional groups throughout; creating chemical groups on the oligonucleotide molecules to interact with the functional groups; and allowing said groups on the oligonucleotide molecules to bond to the functional groups so as to form a homogenous matrix.

Also provided is a method for producing a high volume support, such as a gel substrate, for immobilizing molecules which contain a first chemical moiety, said method comprising supplying a first acrylamide-containing compound; reacting said first compound with a second acrylamide-containing compound having a region which when modified will contain a second chemical moiety capable of interacting with the first chemical moiety; allowing said reaction to proceed sufficiently to produce a copolymer of the first compound and the second compound; and solidifying the polymer on a solid surface.

Also provided is a method for producing arrays of biomolecules comprising modifying the biomolecules to contain an allyl group; polymerizing the biomolecules with acrylamide and/or acrylamide derivatives to create a copolymer mixture; and solidifying the mixture on a solid support.

A method for producing protein arrays is also provided comprising isolating a protein; creating maleimido residues on said protein; reacting said maleimido residues with thiol groups of a bifunctional compound to create a modified protein with acryloyl residues; and polymerizing the modified protein with acrylamide.

A method for immobilizing oligonucleotides is provided comprising reacting an allyl group with the oligonucleotide to form an allyl-oligo complex, and attaching the allyl-oligo complex to a support.

BRIEF DESCRIPTION OF THE DRAWING

The present invention together with the above and other objects and advantages may best be understood from the following detailed description of the embodiment of the invention illustrated in the drawings, wherein:

FIGS. 8A–8C are graphs comparing the degradation kinetics of hydrazide-, amine-, and aldehyde-derived matrices respectively, in accordance with features of the present invention;

DETAILED DESCRIPTION OF THE INVENTION

This invention teaches chemical procedures for modifying polynucleotides for either their direct fluorescent labeling or for their covalent attachment to modified substrates for latter manipulation. The procedures are relatively simple, inexpensive and efficient and have the advantage of being applied to both DNA and RNA either isolated from cells or synthesized.

The procedures are compatible with the fragmentation of nucleic acids. Fragmentation is needed to decrease the formation of hairpin structures that interfere with nucleic acid hybridization to short microchip oligonucleotides. A myriad of lengths of the nucleic acid fragments can be manipulated via the invented processes.

Two processes are disclosed herein, the first dealing with oligonucleotide (e.g. DNA and RNA) labeling and the second dealing with oligonucleotide immobilization. Both processes begin with the modification of oligonucleotide molecules.

I. LABELING PROTOCOL

Several different labels can be incorporated into different nucleic acids for simultaneous multi-color hybridization analysis of the samples.

Several labelling procedures are briefly described herein. A more complete protocol is found in Proudnikov, et al. Nucleic Acids Research 1996 24, 22, pp. 4535–4542, and incorporated herein by reference. Generally, as a first step, chemically active groups, such as aldehyde groups are introduced into DNA by partial depurination (FIG. 1) and into RNA by oxidation of the 3'-terminal ribonucleoside (FIG. 2) with sodium periodate. Fluorescent labels containing a hydrazine group are then coupled with the carbonyl carbon of the aldehyde groups in a nucleophilic addition reaction. The resulting hydrazone bonds are stabilized by reduction with sodium cyanoborohydride.

Figure 3:
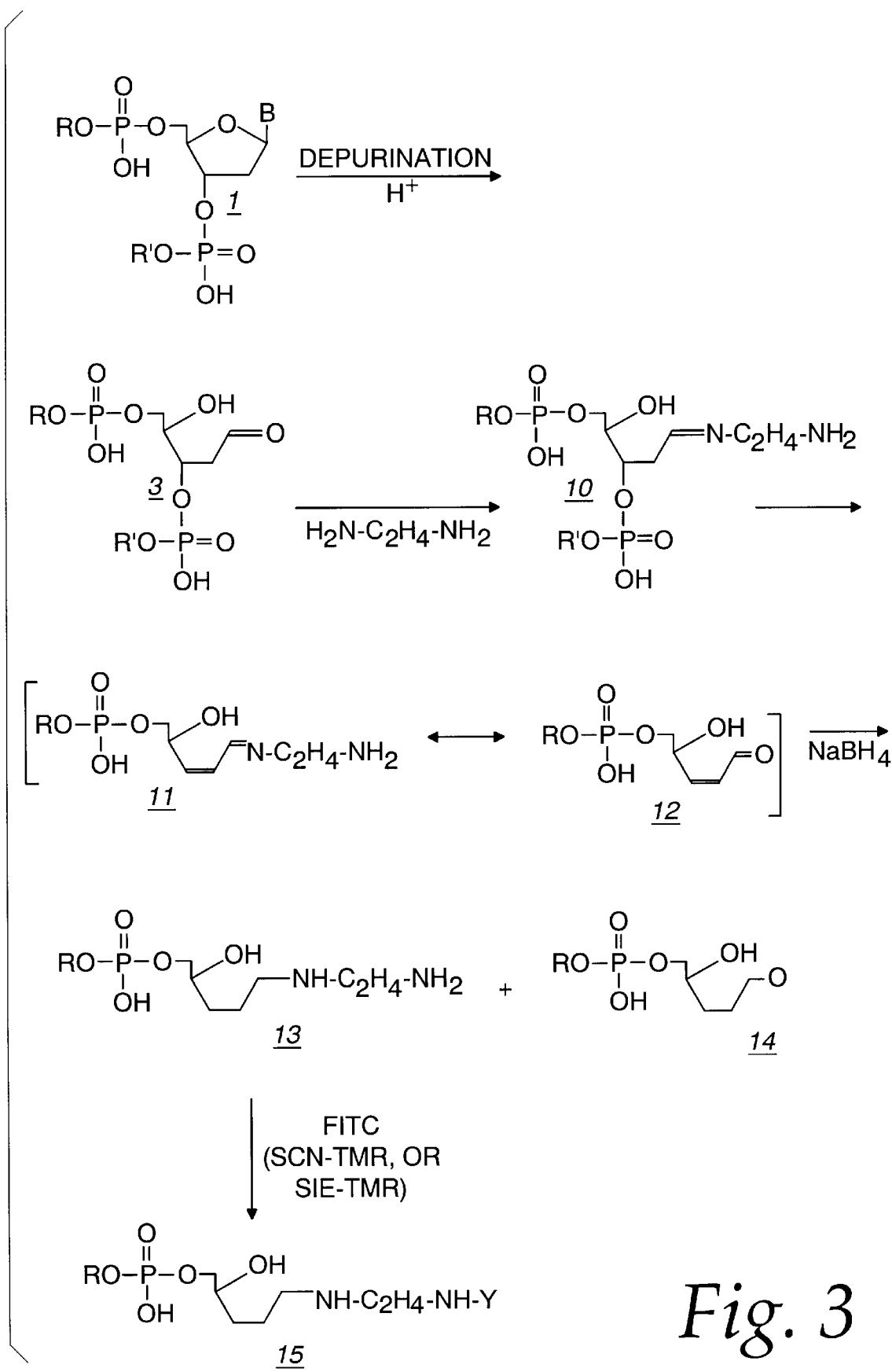
FIG. 3 is an alternative reaction sequence to label DNA, in accordance with features of the invention.

In an alternative method, as depicted in FIG. 3, attachment of ethylenediamine to DNA is followed by preservation of the DNA chain, or its cleavage at the depurinated sites through B-elimination reactions catalyzed by the ethylenediamine. In the presence of reducing agents, such as sodium cyanoborohydride, ethylenediamine forms a stable secondary amine bond with the depurinated site; then activated fluorescent dyes (such as isothiocyanate or succinimide derivatives of the fluorescent dyes) are attached to the second, primary amine group of the bound ethylenediamine. These procedures can be applied for any abasic DNA.

The invented method provides a simple inexpensive process of introducing one fluorescent dye molecule per RNA, as well as the incorporation of labels in either nonfragmented DNA or fragmented DNA. The resulting fluorophores attached to the nucleic acids are stable for use in hybridization experiments. The method can also be used to add other activated agents, for example intercalating agents, to the nucleic acids for subsequent analysis.

A wide range of RNAs, as well as single-stranded and double-stranded DNAs of different lengths were labeled by the invented method and used for hybridization with oligonucleotide microchips. For example, molecules containing more than 1,500 nucleotides are suitable for labeling via the invented labeling process.

Labeling Detail for Depurinated DNA

Figure 1:
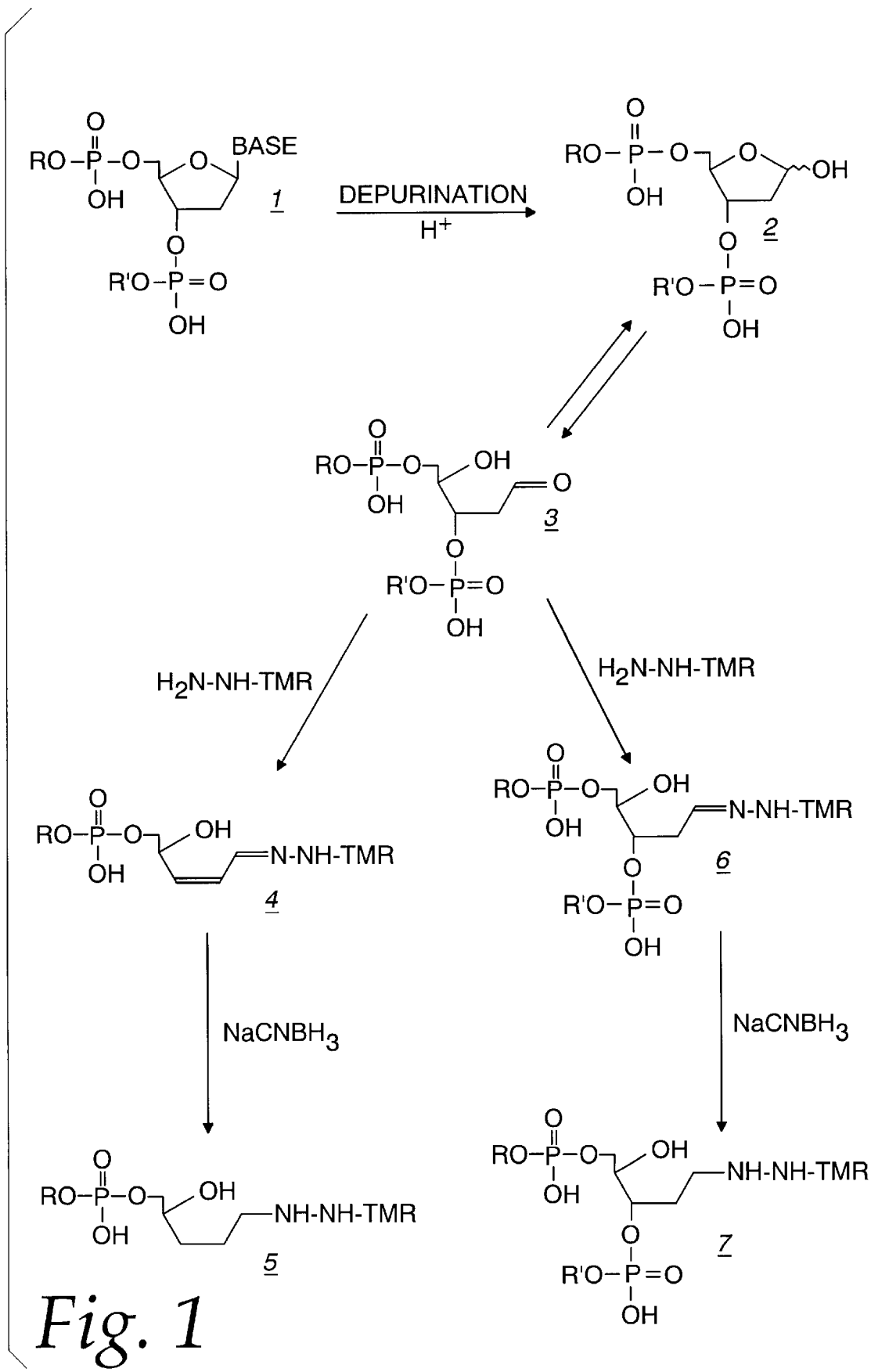
FIG. 1 is a reaction sequence using labeled hydrazine to mark DNA, in accordance with features of the invention.

A scheme for DNA depurination and fluorescent labeling is shown in FIG. 1. As depicted in FIG. 1, depurinated sites in DNA exist in equilibrium in two forms: a cyclic hemiacetal and an open-chain aldehyde. The later species constitutes only about one percent of the species but is highly reactive.

The aldehyde groups react with the hydrazine group of a fluorescent dye. Such dyes include, but are not limited to, tetramethylrodamine (TMR), fluoresceine, Texas Red, Cascade Blue, rhodamine, 4,4-difluoro-4-bora-3a,4a-diaza-s-indacene (e.g. BODIPY™), and combinations thereof. These reagents are commercially available from a myriad of supply houses, including Molecular Probes Inc., Eugene, Oreg. In this particular instance, TMR-hydrazine was used. The synthesis of TMR-hydrazine consists of attachment of bis-hydrazine containing a polyether linker to the fluorophore.

The basic alkylhydrazine group catalyzes β- and δ-elimination reactions that cause DNA fragmentation. The level of fragmentation caused by β-elimination under conditions recited infra varied from 20 to 30 percent and depended on the duration of the reactions.

Double bonds between DNA and the dye are stabilized by reduction with $NaBH_4$, $NaCNBH_3$, or $PyBH_3$. As depicted in FIG. 1, the final product is fluorescently labeled fragmented or non-fragmented DNA.

The efficiency of this method was confirmed via gel electrophoresis wherein it was found that unlabeled oligonucleotides have different electrophoretic mobility than simultaneously-run oligonucleotides labeled with bulky fluorochromes, such as TMR-hydrazine.

Detail of RNA Fluorescent Labeling

The instant invention has considerable utility not only in the labeling of DNA, but also in the labeling of RNA molecules. Two RNA labeling protocols (Path A and Path B) are presented herewith. Little if any preparation of the synthetic or naturally derived oligos is required. For example, if the RNA is phosphorylated at the 3'-terminal position (as the result of fragmentation induced by acids, alkalines, or metals, for example), the phosphate groups can be easily removed by treatment with phosphatase before the following labeling procedures.

Dialdehyde groups are introduced into RNA by oxidation of the 2', 3'-terminal vicinal dihydroxy groups with $NaIO_4$. The resulting carbonyl moieties at the 2' and 3' positions of the sugar can then participate in a nucleophilic addition of the amino groups in TMR-hydrazine, as depicted in path A. The reaction results in a product yield of approximately 60 percent, as depicted in Table 1. An optimal pH range for the reaction is between 3.75 and 4.5.

TABLE 1

Fluorescent Labeling Yields of RNA and DNA by different processes.

| Oligonucleotide | Procedure | Fragmentation % | Yield of labeled Oligo % |
|---|---|---|---|
| 5'-d(T$_6$T$_8$) | TMR-Hydrazine[1] | 20[2] | 59[2] |
| 5'-d(T$_6$T$_8$) | SCN-fluorophore[3] | 87[2] | 55[4, 462] |
| 5'-d(A$_8$Ur) | TMR-hydrazine[1] | | 65[4, 592] |
| 5'-d(A$_8$Ur) | SCN-fluorophore[3] | | 48[4] |

[1]Coupling of TMR hydrazine to depurinated DNA or to 3'-terminal ribonucleotide oxidized with $NaIO_4$.
[2]Yield measured by radioautograph scanning.
[3]Coupling of SCN-fluorophore through ethylenediamine bridge to depurinated DNA or 3'-terminal ribonucleoside oxidized with $NaIO_4$.
[4]Yield was measured by UV-spectroscopy.

Figure 2:
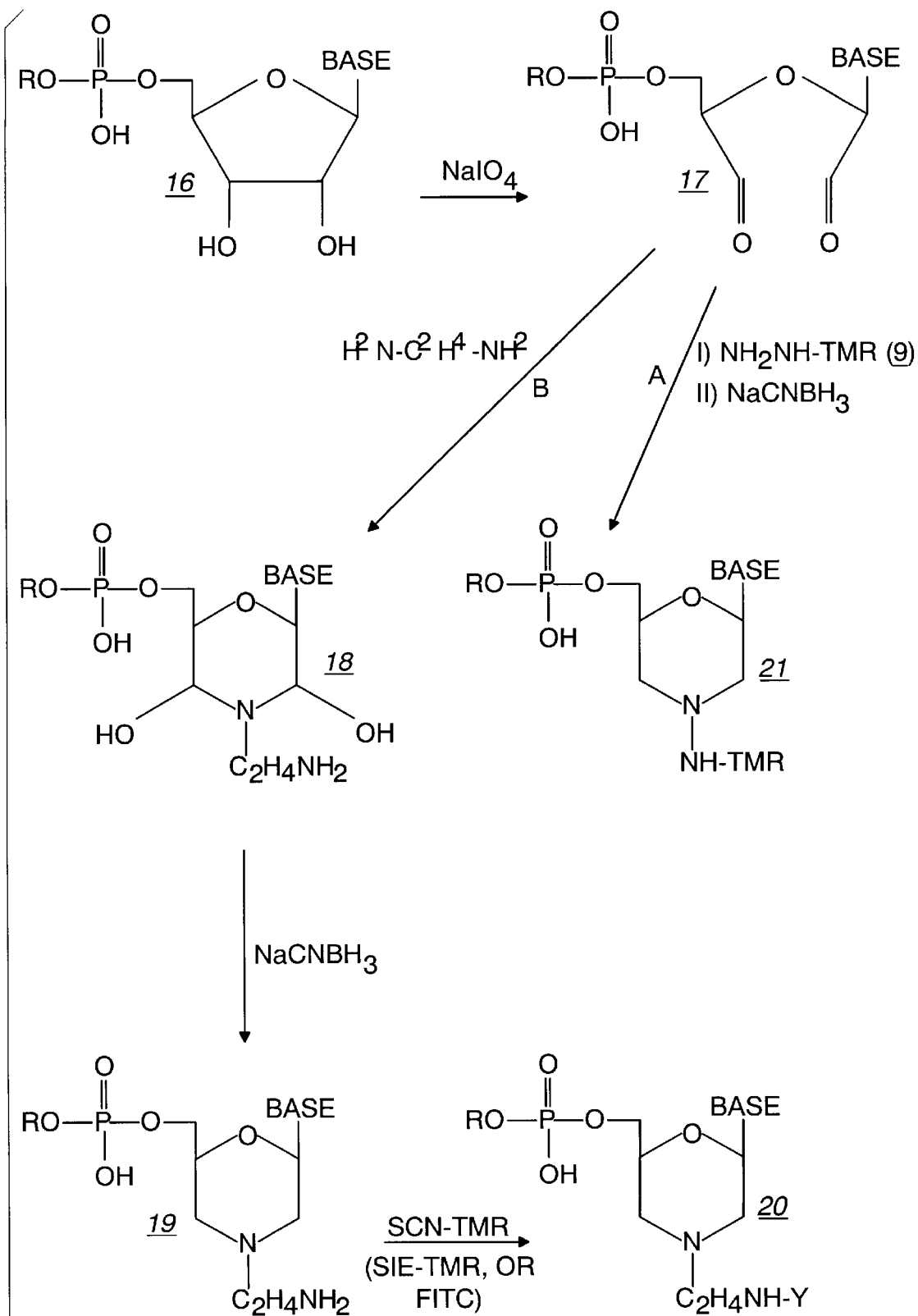
FIG. 2 is a reaction sequence using sodium periodate oxidation to facilitate labeling of RNA, in accordance with features of the invention.

Another RNA labeling process (Path B) calls for ethylenediamine addition to the 3' dialdehyde groups of the oxidized RNA. Activated fluorescein dyes react with the primary amino group of ethylenediamine on the RNA as described below with the alternative labeling procedure of DNA. Path B of FIG. 2 depicts this reactive amino group reacting with fluorophores as FITC (fluorescein isothiocyanate), SCN-TMR (tetramethylrhodamine isothiocyanate), SIE-TMR (tetramethyl-rhodamine succinimide), and Y (fluorophore), to produce the labeled oligo. Yield for this pathway is approximately 50 percent, as depicted in Table 1.

Whether the labeled product is generated via Path A or Path B, the inventors have found that reduction with $NaCNBH_3$ increases its stability.

Detail of Using Ethylenediamine in DNA Labeling Processes

As with the scheme depicted in FIG. 1, this process (FIG. 3) is based on the reductive attachment of chemically active groups or moieties, such as amino compounds, to depurinated DNA.

Ethylenediamine was shown to be particularly effective in the quantitative scission of depurinated DNA, as depicted in FIG. 3. The condensation of ethylenediamine with depurinated DNA sites also introduced a reactive primary amino group that is subsequently used for fluorescent labeling by reaction with commercially available activated fluorophores such as the isothiocyanates or succinimide ethers of fluorescein or tetramethylrhodamine. FIG. 3 depicts these fluorophores as FITC (fluorescein isothiocyanate), SCN-TMR (tetramethylrhodamine isothiocyanate), SIE-TMR (tetramethyl-rhodamine succinimide), and Y (fluorophore).

Label Attachment and Purification Detail

As mentioned supra, the labeling processes taught herein are applicable to both RNA and DNA, either isolated from cells or synthesized in vitro. To facilitate in vitro synthesis of oligos of various lengths, the inventors used a 394 DNA/RNA synthesizer (available through Applied Biosystems, Foster City, Calif.). As with other intricacies of the invented protocol, synthesis detail is provided in Proudnikov et al., noted supra and incorporated herein by reference.

DNA labeling with TMR-hydrazine

Completely depurinated oligonucleotide molecules (10 pmole), either synthesized or isolated, are dissolved in 10 μl of 0.05 M sodium acetate buffer, pH 3.75–5.8 or sodium phosphate buffer, pH 6.5–7.0. In the case of DNA, 10 μg of DNA was dissolved in 10 μl of sodium acetate buffer, pH 4.0.

To the above buffered solutions, 1 μl of 4 mM TMR-hydrazine (i.e. more than a 10-fold molar excess) in 20 percent methanol was added to the reaction mixture. The solution was incubated for 1 hour at 37° C., and then 1.5 μl of 0.2 M $NaCNBH_3$ ($NaBH_4$ or $PyBH_3$) in dry acetonitrile was added and the mixture was incubated at 20° C. for 30 minutes. The mixture was diluted with 100 μl of water and extracted five times with 100 μl of n-butanol saturated with water. The DNA was precipitated with acetone and dried.

RNA Labeling with TMR-hydrazine:

Freshly prepared 0.1 M $NaIO_4$ (1 μl) was added to RNA (up to 20 μg) or to synthetic oligonucleotide molecules in 5 μl of water to create a solution. The solution was incubated at 20° C. for 20 minutes. RNA or the synthetic oligos were precipitated with two percent lithium perchlorate in acetone followed by two washings with acetone. Alternatively, the excess $NaIO_4$ was reduced with 1 μl of 0.2 M sodium hypophosphate for 20 minutes at room temperature.

To the RNA was added 8 μl of 0.1 M sodium acetate, pH 4.0 and 4 mM TMR-hydrazine in 20 percent methanol in the amount of 1 μl per 0.5 nmol of oligonucleotide or fragmented RNA. Coupling was carried out at 37° C. for 1 hour; then 1.5 μl of 0.2 M $NaCNBH_3$ in dry acetonitrile was added and reduction was carried out at room temperature for 30 minutes. The solution was diluted with 100 μl of water, free fluorescent label was extracted with n-butanol, and RNA was precipitated as described above for DNA.

To quantitatively separate fluorescently labeled oligonucleotides from unlabeled ones, the reaction solution was extracted four times with 50 μl of phenol saturated with 1 M Tris-HCl buffer, pH 8. Fluorescently labeled oligonucleotides were precipitated from the combined phenol solutions with a 10-fold excess of 2 percent $LiClO_4$ in acetone.

DNA Labeling via Ethylenediamine Protocol:

Depurinated DNA (up to 10 μg) or 10 pmol of fully depurinated synthetic oligo $[^{32}P]d(T_6GT_8)$ was dissolved in 50 μl of 0.5 M ethylenediamine hydrochloride, pH 7.4, and incubated at 37° C. for three hours. Four microliters of freshly prepared 0.1 M $NaBH_4$ was added at room temperature, followed by incubation at room temperature for 30 minutes. Then, 4 μl of 20 percent ethylenediamine was added to the DNA solution, and the DNA was precipitated with 1 ml of 2 percent lithium perchlorate in acetone, washed twice with acetone, and air-dried. Alternatively, after the 30 minute reduction, the DNA was diluted with 1.5 ml of water, purified on a C18 Sep-Pak cartridge (Waters Corp) eluted with 1 ml of 50 percent methanol, and lyophilized.

The oligonucleotide or DNA with attached ethylenediamine was dissolved in 10 μl of absolute DMSO, and then 1 μl of freshly prepared 3 mM fluorescein (or tetramethylrhodamine) isothiocyanate (or succinimide ether) in dry DMSO and 0.2 μl of triethylamine were added. The reaction mixture was incubated at room temperature for 1 hour and then 80 μl of 0.1 M sodium acetate buffer, pH 4.0 was added. Unreacted fluorescein was extracted five times with 100 μl of water-saturated n-butanol. The DNA was precipitated with acetone and dried.

A protocol for column labeling also has been elucidated by the inventors and is found in the Proudnikov et al. reference noted above and incorporated herein by reference.

RNA Labeling via Ethylenediamine Attachment:

$NaIO_4$-oxidized RNA or synthesized oligo were dissolved in 10 μl of 50 mM sodium acetate buffer (pH 4.0) to which 3 μl of 20 mM ethylenediamine hydrochloride (ph 7.2) was added. After incubation at 37° C. for one hour, 1.5 μl of 200 mM of $NaCNBH_3$ in dry acetonitrile was added at room temperature. Reduction was carried out for 30 minutes, and then RNA (or oligonucleotide) was precipitated with 200 μl of a two percent solution of $LiClO_4$ in acetone and dried. The precipitate was dissolved in 10 μl of dry DMSO, and then 1 μl of a 30 mM solution of fluorescein isothiocyanate in dry DMSO containing 0.2 μl triethylamine was added.

The mixture was incubated at room temperature for 60 minutes and then diluted with 80 μl of 100 mM sodium acetate buffer (pH 4.0). The excess fluorescent label along with traces of fluorescently labeled ethylenediamine was extracted five times with water-saturated n-butanol. The RNA was precipitated with acetone and dried.

In each of the above label-attachment protocols, it will be noted that a high excess of activated fluorescent label is added in the condensation reaction. This is so traces of ethylenediamine, and contaminated RNA and DNA can be ignored. The inventors have found that butanol extraction from acid aqueous solutions substantially separates the labeled product from the excess of unreacted fluorophore without laborious procedures such as dialysis.

Labeled product can be separated from non-labeled oligonucleotide by phenol extraction. This process transfers more than 90 percent of the labeled oligo into the phenol phase, but none of the unlabeled oligo. This is due to the hydrophobic nature of the label. This extraction procedure is particularly suitable for short oligo molecules.

II. FUNCTIONAL GEL PROTOCOL

The inventors have developed a method of forming functional groups on support substrates to facilitate immobilization of oligonucleotides on the support substrates. Generally, functional groups are introduced into a substrate mixture by first copolymerizing typical building-block substrate monomers with compounds which when later modified, provide the functional groups. A number of the protocols disclosed herein allows for the simultaneous formation of functional groups on support substrates and immobilization of oligos on the supports. One final result of the invented processes is the incorporation of both the functional groups and the oligonucleotides as part of the support substrate matrix.

Four types of polyacrylamide or polydimethylacrylamide gels for regio-selective immobilization of short oligonucleotides have been designed for use with modified nucleic acid molecules. Two of these gels (or supports) contain amino or aldehyde groups, allowing for coupling with modified oligonucleotides bearing aldehyde or amino groups, respectively. The other supports are based on an acrylamide gel activated with glutaraldehyde or a hydroxyalkyl-functionalized gel treated with mesyl chloride. The inventors have found that dimethylacrylamide-based supports confers additional utility inasmuch as it facilitates subsequent treatment of the gel with organic solvents and other compounds. As such, the invented process for modifying nucleic acids and gels to facilitate covalent bonding are applicable in either polar or nonpolar environs.

The method for modifying nucleic acids and the subsequent covalent bonding of the nucleic acids to modified gels are more explicitly disclosed in Nucleic Acids Research, 1996, 24,16, pp 3142–3148, and incorporated herein by reference. Briefly, the protocol for modifying gels and subsequent immobilization thereon by modified nucleic acids is as follows:

Generally, functional groups are introduced onto acrylamide-based supports by copolymerization reactions, some of which are depicted in FIGS. 4–7. Two types of gel supports, containing either amines or aldehydes, provide nucleophilic or electrophilic regions to facilitate attachment of oxidized 3' ribo- or aminoalkyloligo-nucleotides, respectively, in the presence of a reducing agent. Exemplary reducing agents include, but are not limited to, sodium cyanoborohydride, pyridine borane, trimethylamine borane or sodium borohydride.

Amine-Containing Substrate Detail

Amino groups are introduced into polyacrylamide and polydimethylacrylamide gels by copolymerization of the corresponding acrylic monomer with ω-aminoalkylacryamide hydrochlorides of the type depicted in formula 1, below:

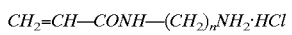

(1)

wherein $6 \geq n \geq 2$.

The two compounds depicted in Formula 1 are prepared by acylation of aliphatic diamines with acryloyl chloride under mild conditions. The number of $NH_2$ groups incorporated into the polyacrylamide gel [1 M gel, 9:1 acrylamide to N-(2-aminoethyl) acrylamide molar ratio] was estimated by staining a 100 μm-thick gel film on a glass side with 2,6-dinitroflurobenzene and analyzing photometrically at 365 nm, inasmuch as glass is transparent at this wavelength. Photometric results revealed that 10 percent of the amino derivative was incorporated into the copolymer. This is suitable for immobilization of between approximately 0.1 to 10 pmol of oligonucleotide in 100×100×20 μm cells.

In several immobilization experiments, dimethylacrylamide was used instead of acrylamide. Polydimethylacrylamide amino matrices were 20 μm thick and had a 0.01 M concentration of amino groups. No additional modifications were carried out with amino matrices except for a short washing with 0.1 M KOH to generate free amines.

Aldehyde-Containing Substrate Detail

Gels containing aldehyde groups for immobilizing nucleic acids modified to contain nucleophilic moieties were also prepared. An exemplary monomer for use in these gels is 5,6—O—isopropylidene-5-6-dihydroxyhexyl) acrylamide, depicted as 11 in FIG. 4.

Figure 4:
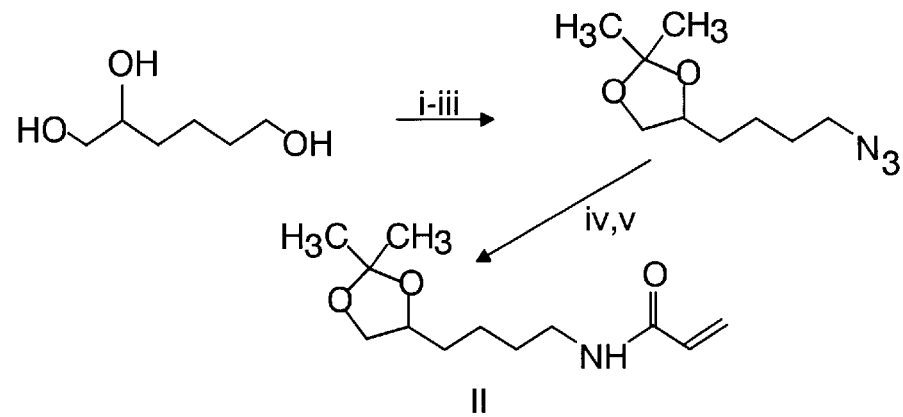
FIG. 4 is a reaction sequence for preparing aldehyde-derivatized support substrates, in accordance with features of the present invention.
Figure 4:
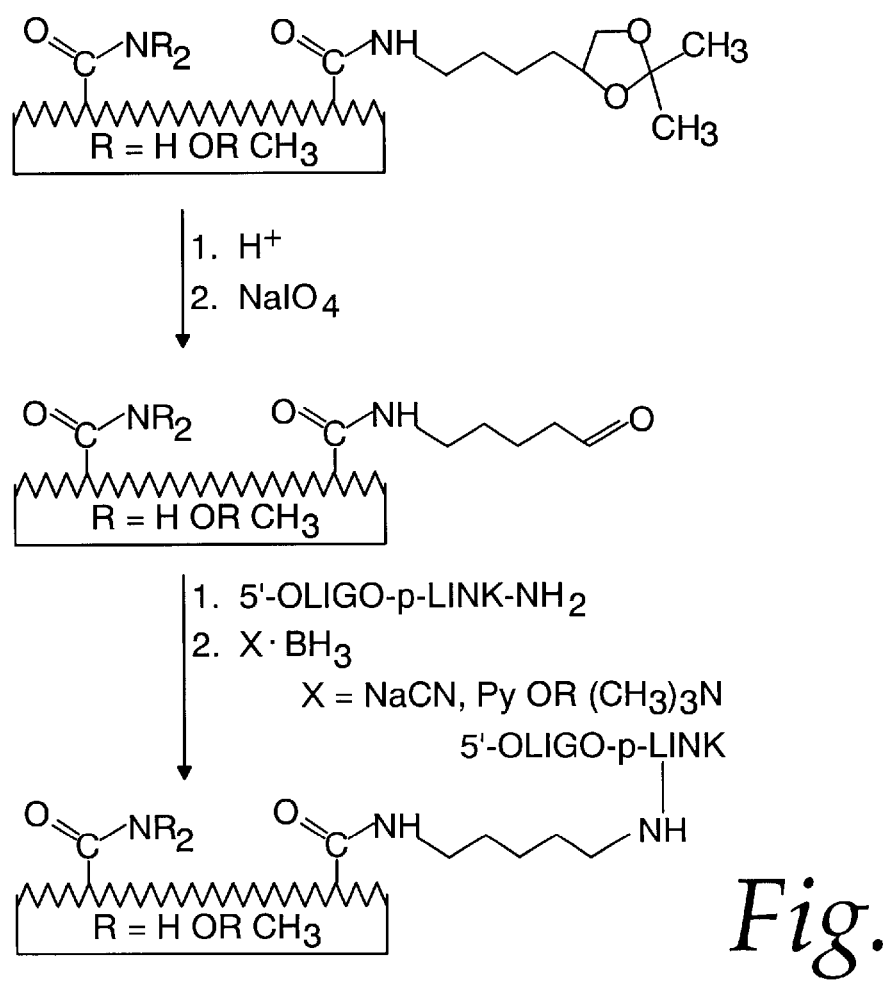
Figure 5:
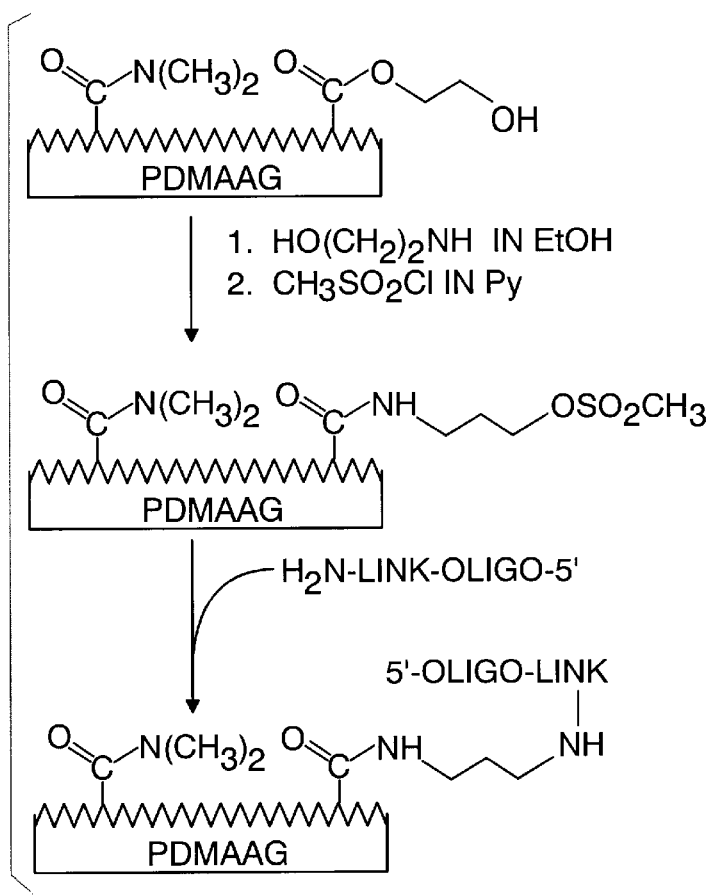
FIG. 5 is a reaction sequence for preparing mesyl-derivatized support substrates, in accordance with features of the present invention.

The synthetic route for preparation of the II monomer is outlined in FIG. 4. (steps i–v.), and fully disclosed in Timofeev, et al, referenced above. Briefly, 1,2,6-trihydroxyhexane was refluxed in a chloroform-acetone mixture in the presence of catalytic amounts of p-toluenesulfonic acid for 6 hours with azeotropic removal of water. The resulting solution was washed with sodium bicarbonate, dried over sodium sulfate and concentrated. The concentrated mixture was reacted with $CH_3SO_2Cl$ at room temperature for 12 hours, quenched with water and then concentrated. This concentrated mixture was dissolved in dry DMF and $LiN_3$ was reacted therewith. The product was organically extracted and then dried. To the dried product was added $Ph_3P$ to facilitate nitrogen release. Aqueous ammonia was added and the resulting solution was kept at room temperature for 12 hours. The resulting product was mixed with triethylamine in dichloromethane and the mixture was added to acryloyl chloride in dichloromethane. The final product, designated as 11 in FIG. 4, was obtained as a viscous liquid.

Dimethylacrylamide was copolymerized with the final product at a 9:1 molar ratio to give an isopropylidene-protected diol function. The gel films were then treated with aqueous acetic acid and 0.1 M $NalO_4$ to produce the final aldehyde matrix.

The inventors have developed other methods for producing aldehyde-containing gel supports. One such method, depicted in Alternate Oxidation Scheme #1, below, combines polyacrylamide gel with diallyl- or diacryloyl-containing cross-linkers (instead of, or in combination with, methylene-bis-acrylamide). As depicted in Alternate Reduction Scheme #1, the inventors have elucidated a possible reaction sequence whereby an exemplary diallyl compound, diallyltartardiamide (DADT) is oxidized (for example by periodate) to two aldehyde-containing moieties, each of which are attached to a gel for subsequent interaction with amine-containing oligos.

Alternate Oxidation Scheme #1

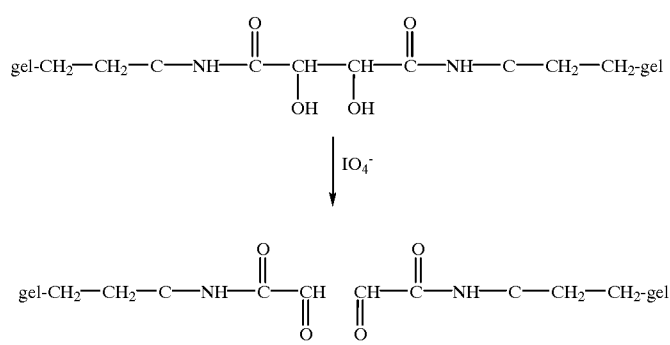

As depicted in Alternate Reduction Scheme #2, below, a possible reaction scenario is where the disulfide group of bisacryloylcysteamide is reduced to yield identical moieties containing sulfhydryl groups at one end available for binding with oligos, while the other end is attached to the gel.

Alternate Reduction Scheme #2

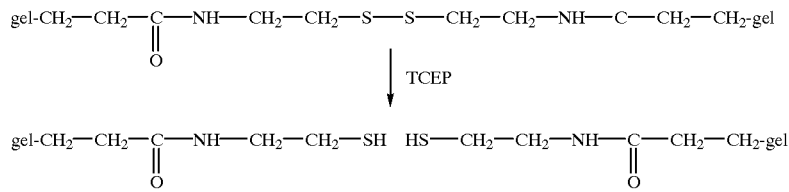

Each of these two additional reagents confer liquid-like or at least more porous gels in as much as the cross-linking at the diol juncture or the disulfide juncture can be controlled. Also, the splitting of the allyl or acryloyl moieties results in the active groups on the free ends of the moieties more readily exposed to solvents and reactive ligands. Indeed, the aldehyde functional group has a long linker which protrudes from the polyacrylamide-chain backbone.

Mesyl- and Glutaraldehyde-Activated Support Substrate Detail

Other types of gel activation are facilitated with copolymers of dimethylacrylamide and β-hydroxyethylacrylate. The β-hydroxy-ethylacrylate, available through Aldrich Chemical, Milwaukee, Wis., facilitates the introduction of hydroxyethyl esters into the gel. The hydroxyethyl group is then selectively substituted by nucleophilic agents such as hydrazine, diamines, amino alcohols and organic amines generally. Briefly, a monomer mixture containing N,N,-dimethylacrylamide, 2-hydroxyethylacrylate, N,N,-methylene-bis-acrylamide and ammonium persulfate is allowed to react to polymerization.

The polymerized gel matrix is then treated with 3-aminopropanol in ethanol and washed with water. After drying, the matrix was treated with $CH_3SO_2Cl$ in dry pyridine. It is this treatment that facilitates the formation of mesyl-activated matrices, depicted in FIG. 5, and hydrazide-activated matrices.

Figure 6:
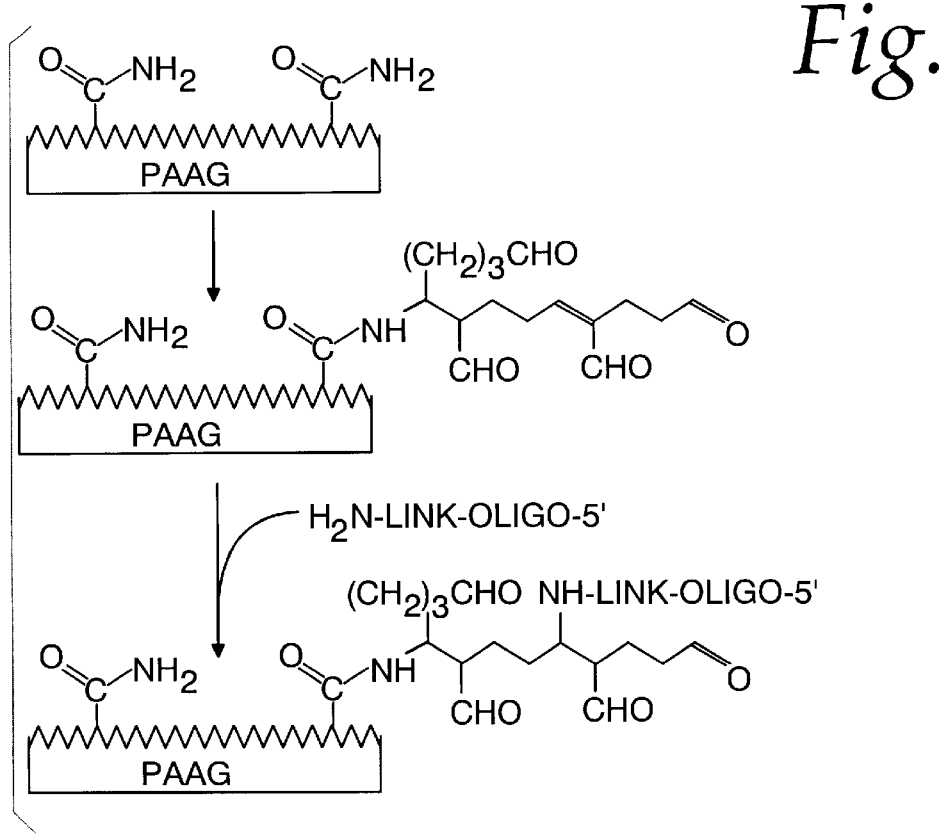
FIG. 6 is a reaction sequence for preparing glutaraldehyde-activated supports, in accordance with features of the present invention.

Glutaraldehyde supports, as depicted in FIG. 6, were also obtained.

The monomer mixture contained acrylamide, N,N-methylene-bis-acrylamide and ammonium persulfate. After gel polymerization, the gel chips were treated with a mixture of glutaraldehyde and phosphate buffer.

Once the functionalized gels are created and gel elements situated on hydrophobic surfaces, the resulting get array is capable of accepting appropriately modified oligonucleotide molecules.

Oligonucleotide Immobilization Detail

Immobilization was carried out with 5'-32P-labeled oligonucleotides: ATGCTACT-X, where X is an oxidized ribose unit from the methyluridine fragment or an $NH_2$ group (oligoR or oligoA, respectively). An amino group was attached to the 3' end of the oligonucleotide through a $C_6$ linker. Unmodified octanucleotide (oligo P) was used as a control. The protocol for modification of the oligos is contained in the Timofeev reference noted supra. Briefly, deoxyoligonucleotides were synthesized on an Applied Biosystems (Foster City, California) synthesizer using phosphoramidite chemistry. N-Me-uridine and amine were used to introduce the methyluridine unit and the amino group into the 3' end of the oligonucleotides, respectively. Purification of the oligos was performed using HPLC.

Figure 7:
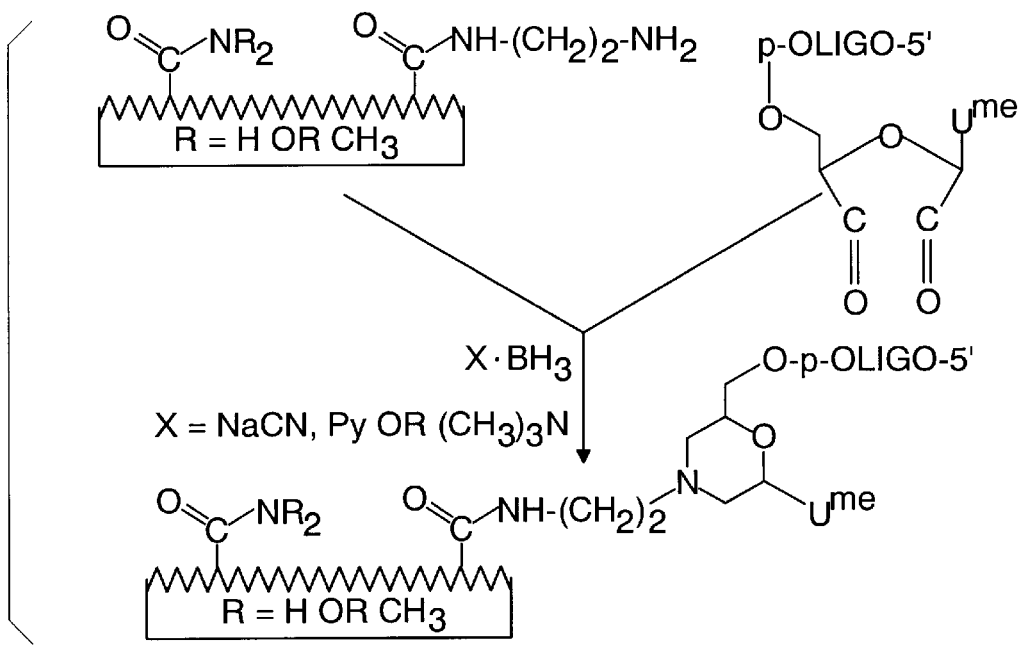
FIG. 7 is a reaction sequence with an amino-functionalized support, in accordance with features of the present invention.

The chemistry of oligo immobilization with simultaneous reduction is shown in FIGS. 4 and 7. Briefly, when amino or aldehyde matrices were used in oligo immobilization, the complementary oligonucleotides (oxidized oligonucleotides for amino supports or amino-oligonucleotides for aldehyde supports) were contacted with a sufficient solution of a reducing agent (such as 0.1 M water solution of $NaCNBH_3$ or $MeSNBH_3$, or a 0.1 M 10 percent aqueous methanol solution for $PyBH_3$) for a sufficient period of time to reduce the oligo-matrix bond. For glutaraldehyde activated matrices, an oligonucleotide (proteins are also suitable) was contacted with the matrix over night at 100 percent humidity. For methane-sulfonate-activated matrices, aminooligonucleotide was mixed in $K_2OO_3$ overnight.

Efficiency of binding was estimated by measuring radioactivity before and after washing in buffer. Both the amino and aldehyde matrices provide fast attachment in high yield. Aldehyde matrices provide relatively higher attachment yields in as much as the carbonyl groups are less likely to react with the radicals needed to form the copolymer chain. Also, the use of the invented aldehyde does not require additional steps for the activation of oligonucleotides (i.e., oxidation of the 3' ribose position) and also makes possible immobilization on the 3' or 5' end. As noted supra, sodium cyanoborohydride, pyridine-borane and trimethylamine-borane complexes, among others, were used as reducing agents in aldehyde-matrix scenarios, as depicted in FIG. 7. Particularly good results were obtained when the pyridine-borane complex was utilized.

As can be noted in FIG. 6, the activation of the glutaraldehyde supports involves the reaction of the relatively inert amide groups of the support with the bifunctional glutaraldehyde trimer. This type of activation gives good results in the immobilization of proteins and can be successfully applied to the preparation of protein microchips.

FIGS. 8A–8C illustrate the relative stability of functionalized oligo supports. The stability of the matrices was measured in 0.1 M triethylammonium acetate buffer, pH 7.0 at 60° C. For each immobilized oligonucleotide, the decrease in radioactivity was monitored in three spots, each 1 mm in diameter. For every spot, eight measurements were made using a digital radioactive monitor. The experimental data are presented by mean points and error bars. The straight line is the fitting curve and the dashed line is the curve of the initial fast breakdown.

The relative stability of the various functionalized supports is depicted in FIG. 8. FIG. 8A depicts the degradation of matrices obtained by the condensation of a hydrazide matrix with oligonucleotide containing a dialdehyde group. FIG. 8B depicts the kinetics of an amine matrix with oligonucleotide containing a dialdehyde group with reduction by pyridine-borane complex. FIG. 8C depicts the degradation kinetics of an aldehyde matrix with oligonucleotide containing an amino group with reduction by pyridine-borane complex.

As can be seen in FIG. 8, the stability of easily hydrolyzable bonds such as hydrazone or imine (FIG. 8A) is much less than the aminoalkyl bonds conferred with the invented functionalized gels FIGS. 8B and 8C.

Table 2 below illustrates the efficiency of the various functionalized gels in the immobilization of oligos containing nucleophilic moieties (i.e. amino groups) and of oligos containing electrophilic moieties (i.e. carbonyl groups. As Table 2 illustrates, gel supports containing aldehyde moieties as attachment sites for modified oligos provide superior immobilization efficiencies.

Table 2: Efficiency of immobilization for certain functionalized gels:

TABLE 2

Efficiency of immobilization for certain functionalized gels:

| Support: active group (reductant) | Oligonucleotide (active group) | FIGS showing preparation | Yield (%) | Nonspecific binding (%) |
|---|---|---|---|---|
| —$NH_2$(NaCN.$BH_3$) | OligoR (—CHO) | 6 | 60 ± 5 | 2 ± 1 |
| —$NH_2$ (Py.$BH_3$) | OligoR (—CHO) | 6 | 74 ± 5 | 5 ± 1.5 |
| —$NH_2$($Me_3$N.$BH_3$) | OligoR (—CHO) | 6 | 68 ± 5 | 3 ± 1 |
| —CH=O(NaCN.$BH_3$) | OligoA (—$NH_2$) | 7 | 95 ± 5 | 9 ± 2 |
| —CH=O(Py$BH_3$) | OligoA (—$NH_2$) | 7 | 97 ± 5 | 8 ± 2 |
| —CH=O($Me_3$N$BH_3$) | OligoA (—$NH_2$) | 7 | 94 ± 5 | 3 ± 1 |
| —$OSO_2$Me | OligoA (—$NH_2$) | 5 | 35 ± 5 | 0 ± 0.5 |
| Glutaraldehyde | OligoA (—$NH_2$) | 4 | 71 ± 5 | 17 ± 3 |
| —C(O)—NH—$NH_2$† | OligoR (—CHO) | | 87 ± 5 | 1 ± 0.5 |
| —C(O)—NH—$NH_2$‡ | OligoR (—CHO) | | 88 ± 5 | 1 ± 0.5 |

†Standard hydrazide matrix; ‡(2-hydroxyethyl)acrylate copolymer derived by hydrazine.

Aside from immobilizing oligos via interactions with functional groups in already formed gel elements, the inventors have also found that molecules (such as nucleic acids, proteins, and oligonucleotides) also can be incorporated as part of the copolymers that comprise the substrate matrix.

Protein Immobilization/Gel Incorporation Detail

The inventors have developed a technique of copolymerizing modified proteins with gel-forming monomers. This technique obviates the current drawbacks associated with protein immobilization on gel cells wherein diffusion of the proteins into gel elements are slow due to the size of the protein. By incorporating proteins as part of the gel matrix, microchips are obtained for use in antigen-antibody binding, in studying the interactions between proteins and low molecular weight compounds and other bio-active substances. Universal diagnostic chips can be developed whereby antigens from a genomic library can be immobilized for subsequent screening of possible antibodies.

One method, elucidated by the inventors, for interlacing proteins into a gel matrix is as follows: Amino groups of proteins are modified to contain maleimido residues. One such path for the modification is by allowing the proteins to react with succinimidyl residues of a heterobifunctional reagent. One such reagent is sulfosuccinimidyl-4-(N-maleimidomethyl) cyclohexane-1-carboxylate (SMCC), available through Pierce Chemical Company of Rockford, Ill. The maleimido residues are contacted with thiol groups in the PAAG, the thiol groups first formed via reduction of the disulfide moieties contained in the cross-linkers of the PAAG. Typical bifunctional cross-linkers utilized by the inventors include bis N,N'-acryloylcysteamine, which is commercially available from BioRad, Hercules, Calif. Reduction of the disulfide bond was facilitated rapidly (within minutes) by Tris-(2-carboxyethyl) phosphine-HCl, also available from Pierce Chemical.

The modified protein, with its acryloyl residues, can participate in the polymerization of acrylamide gel as a kind of gel-forming monomer. Each protein molecule can have several acryloyl residues.

Figure 9:
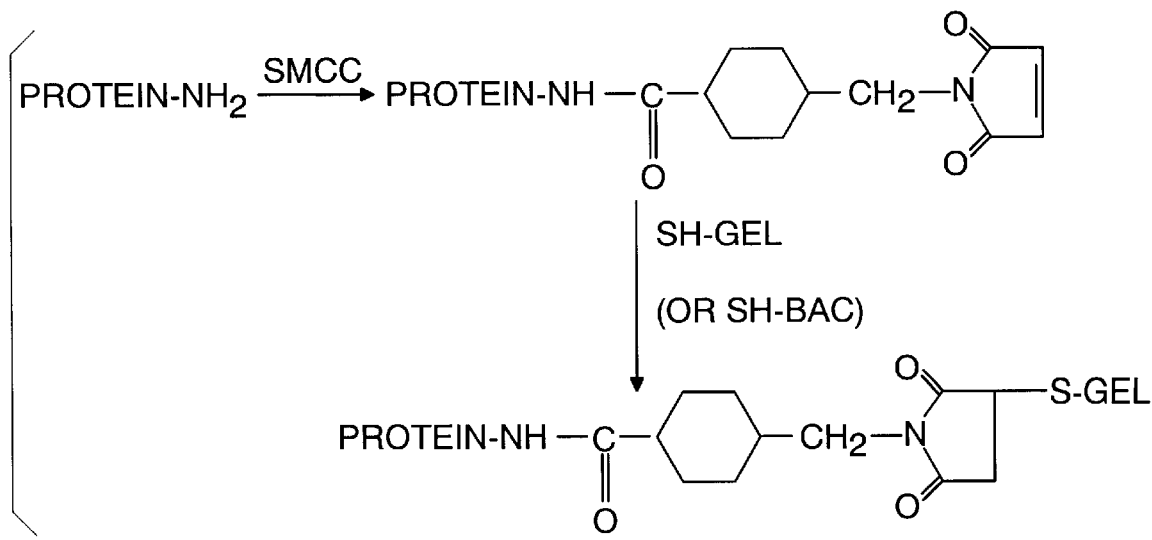
FIG. 9 is a reaction sequence of an activated protein for incorporation into an acrylamide matrix, in accordance with the present invention.

Modification of protein via SMCC is depicted in FIG. 9, and generally proceeds as follows: To a protein, in this case 66 μl of streptavidin (3.3 nmol) in water was added 10 μl of 1 M HEPES, pH 7.5, 23 μl of water, and 2.0 μl (36 nmol) SMCC in DMSO. The reaction mixture was incubated at 4° C. Excess reagent was removed on a Sephadex G-25 column equilibrated with 10 mM of MES, pH 6.2, and the protein was concentrated by centrifugation in centricon 30 (by Amicon, Beverly, Mass.).

The SMCC-modified proteins were used immediately for conjugation with reduced BAC. (BAC was first reduced by treating a solution of 10 μmol BAC in 0.5 ml 20 mM MES buffer, pH 6.2 with 1.2 molar excess of TCEP for 10 minutes at room temperature.) The SMCC-modified proteins were treated with a 50-fold molar excess of reduced BAC for 1 hour. Proteins were purified from unreacted component by gel filtration on Sephadex G-25. The inventors have determined that one protein molecule can be modified by multiple acryloylcysteamine groups.

After the acryloyl-modified protein is produced, protein chips are then manufactured via the following method: The polymerization mixture contained 31 μl of acrylamide stock solution (40 percent (w/v) acrylamide, 2 percent bis acrylamide); 80 μl of glycerol; 3 μl of TEMED;

10 μl of 1 M-tris HCl, pH 8.0; 9.3 μl of 9 percent HCl; 0.5 μl of 0.5 M EDTA; 12.5 μl of 0.05 percent Methylene Blue in water; and 5–20 1 solution of the acryloyl-modified protein (100–400 pmol), with water added to a final 250 μl volume.

The resulting mixture is then irradiated (UV light at 254 nm to 300 nm) for a period sufficient to solidify the gel pads. Thirty minute irradiation times produce acceptable gel pads. The size of gel pads vary from 40 μm to 1 mm.

The pads are then washed to remove unpolymerized protein. Typical wash protocol is a 10 minute water wash, a 1× PBS with 0.1 percent Tween 20 wash for 10 minutes, and then a 10 minute binding buffer wash. Then the chip is incubated with large access of buffer for two days with constant agitation.

The characterization of the produced protein microchips revealed that unambiguous conjugate signals with biotin-fluorescein are obtained. Particularly good results have been obtained when as little as 40–160 Atom moles of immobilized protein are utilized.

Allyl-modified Oligonucleotide Detail

The inventors have also developed another immobilization substrate material consisting of a copolymer of allylic monomers with acrylamide and bisacrylamide. In one instance, the allylic monomers, such as allylic phosphoramidite, are first attached to the oligos at the 3' or the 5' ends or anywhere in between, and then the oligos are subsequently copolymerized with acrylamide-bisacrylamide mixture. For example, the allylic group —CH—CH=$CH_2$ in an oligonucleotide participates in a copolymerization reaction with acrylic monomers $CH_2$=CH—C(O)—X (wherein X=$NH_2$, $OCH_2CH_2OH$, $N(CH_3)_2$, HN—$CH_2$—NH—(O) C—CH=$CH_2$ or some other acrylic derivative) under UV light, visible light or by action of radical initiators.

Figure 10:
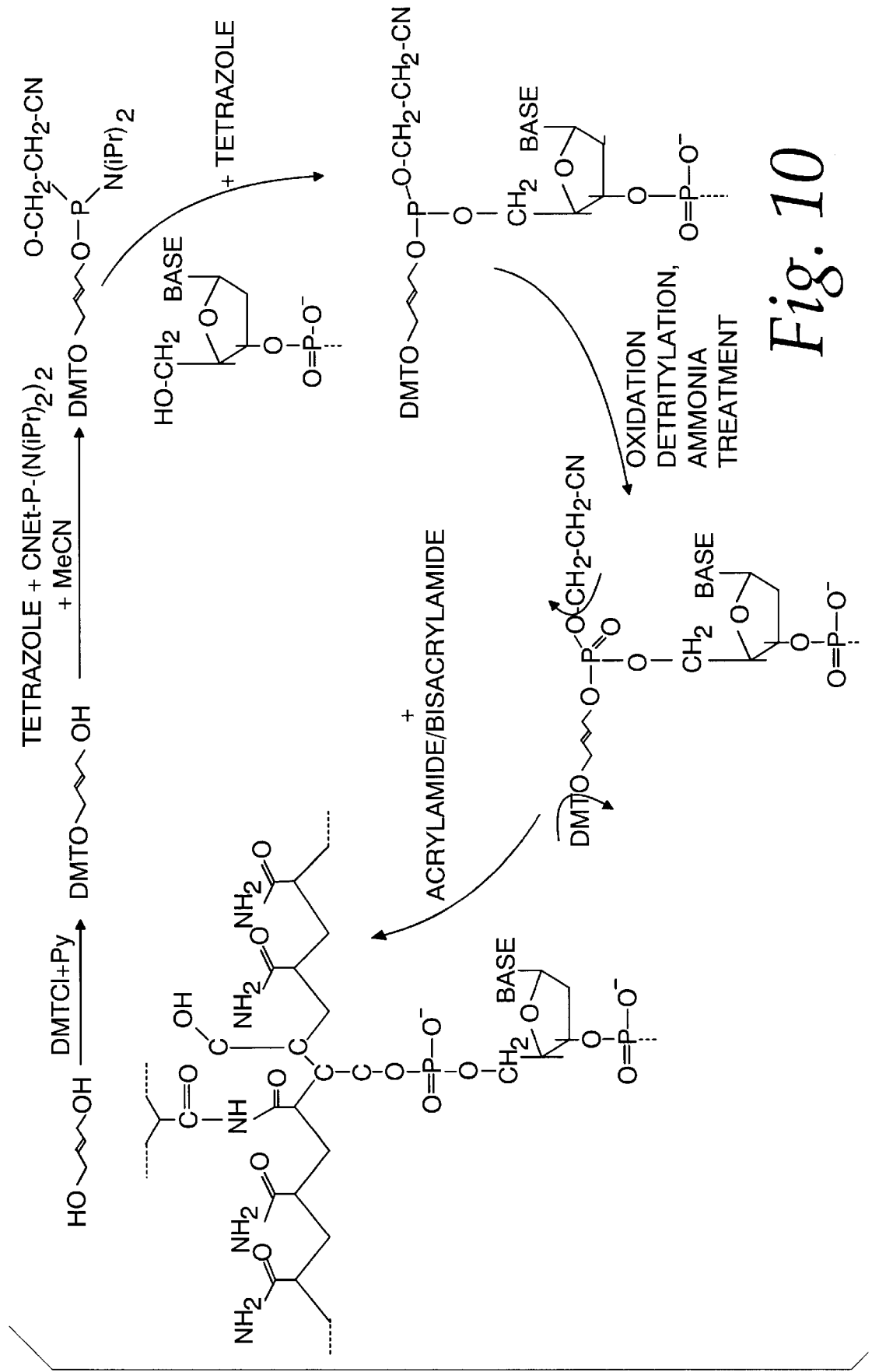
FIG. 10 is a reaction sequence of an allyl-modified oligo that is incorporated into a support matrix, in accordance with features of the present invention.

Allylic phosphoramidite, prepared via the reaction sequence depicted in FIG. 10, allows for the incorporation of its active allyl group into any position of an oligonucleotide. Briefly, the phosphoramidite is synthesized by reacting an excess of 2-buten-1,4-diol with a mixture of dimethoxytrityl chloride (DMTCl) and pyridine (Py). A diol:DMTCL mole ratio of 3:1 in pyridine at room temperature for two hours is suitable. The resulting dimethoxytrityl-butene (in this instance 1-(4,4'-dimethoxy)-triphenylmethoxy-2-butene-4-ol) is then reacted with 2-cyanoethyl-tetraisopropyl-phosphoramidite (CNet-P-(N(iPr)$_2$)$_2$ and tetrazole in acetonitrile (MeCN), or some other suitable solvent. This results in the formation of a tritylated allyl complex.

Once the phosphoramidite complex is attached to the oligo, the resulting tritylated allyl-oligo complex is treated to oxidize the phosphorous contained on the phosphramidite molecule. The complex is also detritylated, (in this instance the DMT is removed from the 5' end of the oligo complex), thereby allowing for the formation of a hydroxyl group to facilitate oligo chain elongation. It is the provision of this hydroxyl group that allows for positioning an allylic group in the middle of a growing oligo chain. Furthermore, the DMT moiety is also removed to stymie possible hydrophobic effects it might promote. Ammonia treatment is one suitable method for both cleaving the DMT group from the 5' end and also to cleave the 3' end of the oligo from whatever support is utilized during the chain-building process, one such support being controlled pore glass.

The resulting allyl-oligonucleotide complex can then be copolymerized with acrylic monomers to yield a gel substrate interlaced with the oligo. The place or attachment of particular oligonucleotides on particular regions of a gel are facilitated via photopolymerization. Alternatively, further elongation of the oligo chain can occur, to as to result in the chain having an allyl group at other than its terminal ends, with subsequent gel attachment.

The oligo-chain lengthening process can be facilitated with the use of oligonucleotide synthesizers, such as those available from Applied Biosystems Inc., Foster City, Calif., including the ABI-394.

Also, aside from the butene monomer depicted in FIG. 10, other monomers having double bond structure also are suitable constituents, including those having the general structure depicted below:

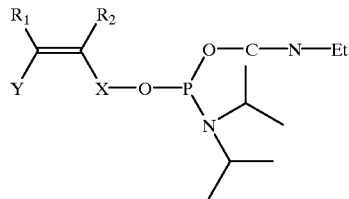

where R$_1$=H, alkyl, aryl, and halogen; R$_2$=H, alkyl, aryl, and halogen; X=alkyl; and Y=H, alkyl, DMTO-alkyl.

EXAMPLE

Four squares, 1×1 mm of cross-linked acrylamide-bisacrylamide-allyl-oligonucleotide copolymer were prepared by photopolymerizations of mixtures of acrylamide and bisacrylamide with four different allyl-oligonucleotides. The copolymerization was carried out as follows: Four different oligonucleotide solutions (0.3 mM oligonucleotide in 4 percent AA-bis, 19:1, 0.1 M phosphate buffer in 40 percent glycerol, pH 7, TEMED, and methylene blue) were each and separately copolymerized under UV light using a 1×1 mm mask with washing between copolymerizations.

After completion of polymerization the resulting 2×2 microchip was washed in water at 60° C. for three hours and hybridized with complementary labeled oligonucleotides. Each allyl-oligonucleotide differed from one another by a single base change in the middle of its sequence. Specific binding of labeled target to one of four cells was observed in each hybridization.

It is noteworthy that hybridization endeavors disclosed throughout all portions of this teaching can be facilitated by including nucleotide analogs, such as universal bases, into either the target sequence or the immobilized fraction of oligonucleotides, DNA and/or RNA. Such universal bases as 5-nitroindole, 3-nitropyrrole, inosine, among others, are suitable candidates.

While the invention has been described with reference to details of the illustrated embodiment, these details are not intended to limit the scope of the invention as defined in the appended claims.

The embodiment of the invention in which an exclusive property or privilege is claimed is defined as follows:

What is claimed:

1. A method for attaching oligonucleotides to polyacrylamide comprising:
    a) providing a compound with both vicinal diols and an acrylic function;
    b) protecting the vicinal diols to form a first acrylic monomer;
    c) polymerizing said first acrylic monomer of step b with a second acrylic monomer;
    d) deprotecting the vicinal diols in said polymer;
    e) oxidizing the vicinal diols to form a free aldehyde group in said polymer;
    f) condensing a free primary amino group of the oligonucleotide with the aldehyde to form a Schiff's base, and
    g) reducing the Schiff's base to yield a stable covalent bond between the oligonucleotide and said polymer.

2. The method of claim 1, wherein the vicinal diol is a cis diol.

3. The method of claim 1, wherein said vicinal diol protecting group is isopropylidene.

4. The method of claim 1, wherein the Schiff's base is reduced with a borane complex.

5. The method of claim 1, wherein the Schiff's base is reduced with a borane complex having the formula X BH$_3$ wherein X is selected from the group consisting of sodium cyanide, pyridine, and trimethylamine.

6. A method for attaching a modified oligonucleotide to acrylamide comprising:
    a) providing an oligonucleotide with a phosphoramidite having one hydroxyl protected with an alkene protecting group whose own hydroxyl group is protected with a trityl group;
    b) deprotecting the other phosphoryl hydroxyl group of said phosphoramidite;
    c) detritylating the hydroxyl of the allyl group; and
    d) polymerizing the above modified oligonucleotide with a second acrylic monomer.

7. The method of claim 6, wherein said phosphoramidite is attached to the oligonucleotide at the 3'-end, or the 5'-end, or at any internucleotide position.

8. The method of claim 6, wherein said second acrylic monomer is selected from the group consisting of CH$_2$=CH—C(O)—NH$_2$, CH$_2$=CH—C(O)—OCH$_2$CH$_2$OH, CH$_2$=CH—C(O)—N(CH$_3$)$_2$, and CH$_2$=CH—C(O)—HN—CH$_2$—NH$_2$—(O)C—CH=CH$_2$.

9. The method of claim 6, wherein said second acrylic monomer is acrylamide or bisacrylamide.

10. The method of claim 6, wherein said alkene hydroxyl protecting group is 2-buten-1,4-diol.

* * * * *

UNITED STATES PATENT AND TRADEMARK OFFICE
CERTIFICATE OF CORRECTION

Page 1 of 2

PATENT NO. : 5,981,734
DATED : November 9, 1999
INVENTOR(S) : Mirzabekov et al.

It is certified that error appears in the above-identified patent and that said Letters Patent is hereby corrected as shown below:

Detailed Description of the Invention, paragraph 15, column 5, line 39, after the word "with" delete "$NaIO_4$" and insert the word --$NaIO_4$--.

Table 1, line 54, replace "$55^{4,462}$" with --$55^4$, $46^2$--.

Table 1, line 55, replace "$65^{4,592}$" with --$65^4$, $59^2$--.

Detailed Description of the Invention, column 10, line 9, after the word "M" delete "$NaIO_4$" and insert the word --$NaIO_4$--.

Detailed Description of the Invention, column 10, line 50, replace

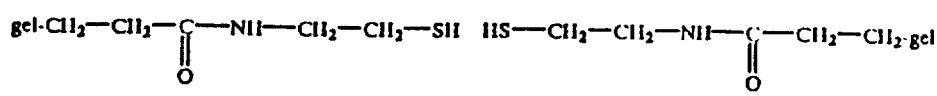

UNITED STATES PATENT AND TRADEMARK OFFICE
CERTIFICATE OF CORRECTION

PATENT NO. : 5,981,734
DATED : November 9, 1999
INVENTOR(S) : Mirzabekov et al.

It is certified that error appears in the above-identified patent and that said Letters Patent is hereby corrected as shown below:

with

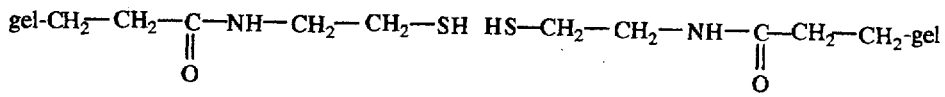

Detailed Description of the Invention, column 11, line 54, after the word "or", first occurrence, delete "MeSNBH$_3$" and insert the word --Me$_3$NBH$_3$--.

Signed and Sealed this

Tenth Day of October, 2000

Attest:

Attesting Officer

Q. TODD DICKINSON

Director of Patents and Trademarks